US006010694A

United States Patent [19]

Siracusa et al.

[11] Patent Number: 6,010,694

[45] Date of Patent: Jan. 4, 2000

[54] FIBRILLIN 1 GENE COMPRISING DUPLICATION MUTATION AND COMPOSITIONS AND KITS USING THE SAME

[75] Inventors: Linda D. Siracusa, Cherry Hill, N.J.; Sergio A. Jimenez, Philadelphia, Pa.

[73] Assignee: Thomas Jefferson University, Philadelphia, Pa.

[21] Appl. No.: 08/687,967

[22] Filed: Jul. 26, 1996

Related U.S. Application Data

[60] Provisional application No. 60/001,561, Jul. 27, 1995.

[51] Int. Cl.[7] .......................... A01N 63/00; C07H 21/04; C12N 5/00

[52] U.S. Cl. .................... 424/93.21; 536/23.1; 536/23.5; 435/366

[58] Field of Search ............................... 424/93.1, 93.21; 514/44; 536/23.1, 23.6, 23.5; 435/235, 325, 366

[56] References Cited

U.S. PATENT DOCUMENTS

| | | | |
|---|---|---|---|
| 4,645,669 | 2/1987 | Reid | 424/95 |
| 4,703,108 | 10/1987 | Silver et al. | 530/356 |
| 4,736,866 | 4/1988 | Leder et al. | 800/1 |
| 4,873,191 | 10/1989 | Wagner et al. | 435/172.3 |
| 5,334,527 | 8/1994 | Brysk | 435/240 |
| 5,376,118 | 12/1994 | Kaplan et al. | 623/11 |

OTHER PUBLICATIONS

Aoyama, et al., "Quantitative Differences in Biosynthesis and Extracellular Deposition of Fibrillin in Cultured Fibroblasts Distinguish Five Groups of Marfan syndrome Patients and Suggest Distinct Pathogenetic Mechanisms", *J. Clin. Invest.*, 1994, 94(1), 130–137.

Christiano, et al., "Molecular Pathology of the Elastic Fibers", *J. Invest. Dermatol.*, 1994, 103(5), 53S–57S.

Francke, et al., "A Gly1127Ser Mutation in an EGF–like Dmain of the Fibrillin–1 Gene is a Risk Factor for Ascending Aortic Aneurysm and Dissection", *Am. J. Hum. Genet.*, 1995, 56(6), 1287–1296.

Handford, et al., "The Calcium Binding Properties and Molecular Organization of Epidermal Growth Factor–like Domains in Human Fibrillin–1", *J. Biol. Chem.*, 1995, 270(12), 6751–6756.

Rantamaki, et al., "Prenatal Diagnosis of Marfan Syndrome Identification of a Fibrillin–1 Mutation in Chorionic Villus Sample", *Prenatal Diagnosis*, 1995, 15(12), 1176–1181.

Aoyama, T., et al., "Missense mutations impair intracellular pocessing of fibrillin and microfibril assembly in Marfan syndrome", *Human Molecular Genetics*, 1993, 2, 2135–2140.

Cleary, E.G. and Gibson, M.A., "Elastin–Associated Microfibrils and Microfibrillar Proteins", *Int. Rev. Connect. Tiss. Res.*, 1983, 10, 97–209.

Corson, G.M., et al., "Fibrillin Binds Calcium and Is Coded by cDNAs That Reveal a Multidomain Structure and Alternatively spliced Exons at the 5'End", *Genomics*, 1993, 17, 476–484.

Dietz, H., et al., "Marfan syndrome caused by a recurrent de novo missense mutation in the fibrillin gene", *Nature*, 1991, 352, 337–339.

Dietz, H., et al., "Marfan Phenotype Variability in a Family Segregating a Missense Mutation in the Epidermal Growth Factor–like Motif on the Fibrillin Gene", *J. Clin. Invest.*, 1992, 89, 1674–1680.

Dietz, H., et al., "Clustering of Fibrillin (FBN1) Missense Mutations in Marfan Syndrome Patients at Cysteine Residues in EGF–Like Domains", *Human Mut.*, 1992, 1, 366–374.

Goldstein, C., et al., "Of mice and Marfan: genetic linkage analyses of the fibrillin genes, Fbn1 and Fbn2, in the mouse genome", *Mamm. Genome*, 1994, 5, 696–700.

Jablonska, S., et al., "Conjenital fascial dystrophy: Stiff skin syndrome–a human counterpart of the tight–skin mouse", *J. Am. Acad. Derm.*, 1989, 21, 943–950.

Jimenez S. and Christner, P., "Animal Models of Systemic Sclerosis", *Clinics Derm.*, 1994, 12, 425–436.

Kainulainen, K., et al., "Two mutations in Marfan syndrome resulting in truncated fibrillin polypeptides", *Proc. Natl. Acad. Sci. USA*, 1992, 89, 5917–5921.

Lee, B., et al., "Linkage of Marfan syndrome and a phenotypically related disorder to two different fibrillin genes", *Nature*, 1991, 352, 330–334.

Maslen, C.L., et al., "Partial sequence of a candidate gene for the Marfan syndrome", *Nature*, 1991, 352, 334–337.

Pereira, L., et al., "Genomic organization of the sequence coding for fibrillin, the defective gene product in Marfan syndrome", *Hum. Mol. Genet.*, 1993, 2, 961–968.

Yin, W., et al., "Primary Structure and Developmental Expression of Fbn–1, the Mouse Fibrillin Gene", *J. Biolog. Chem.*, 1995, 270, 1798–1806.

Sakai, L.Y., et al., "Fibrillin, A New 350–kD Glycoprotein, as a Component of Extracellular Microfibrils", *J. Cell. Biol.*, 1986, 103, 2499–2509.

Gibson, M.A., et al., "The Protein Components of the 12–Nanometer Microfibrils of Elastic and Nonelastic Tissues", *J. Biol. Chem.*, 1989, 264, 4590–4596.

Ramirez, F., et al., "The Fibrillin–Marfan Syndrome Connection", *Bioessays*, 1993, 15, 589–594.

Orkin et al. (NIH panel report) Report and recommendations of the panel to assess the NIH investment in research on gene therapy, Distributed by the National Institutes of Health, Bethesda, MD, Dec. 7, 1995.

*Primary Examiner*—Brian R. Stanton
*Assistant Examiner*—Deborah J. R. Clark
*Attorney, Agent, or Firm*—Woodcock Washburn Kurtz Mackiewicz & Norris LLP

[57] ABSTRACT

Human fibroblast cells that comprise a gene construct that comprises a duplication mutated fibrillin 1 gene operably linked to functional regulatory elements and compositions comprising such cells are disclosed. Methods of treating wounds and kits for practicing such methods are disclosed. Transgenic animals comprising a duplication mutated fibrillin 1 gene operably linked to a tissue specific and/or inducible promoter are disclosed. Methods of identifying individuals with a duplication mutated fibrillin 1 gene are disclosed. The methods comprises detecting a duplication of exons 17–40 of a fibrillin 1 gene or a gene product produced by expression of a duplication mutated fibrillin 1 gene. Methods of preventing expression of a duplication mutated fibrillin 1 gene are disclosed.

11 Claims, 7 Drawing Sheets

```
                                  ↓
5' GTG AAC GGG GGA AAT AAT TGC ATG GCG GAA TAT CAG GCA CTC TGC AGC AGT 3'
   CAC TTG CCC CCT TTA TTA ACG TAC CGC CTT ATA GTC CGT GAG ACG TCG TCA
```

FIG. 5B

```
                                  ↓
Val Asn Gly Gly Asn Asn Cys Met Ala Glu Tyr Gln Ala Leu Cys Ser Ser

         Exon 40                              Exon 41
Val Asn Gly Gly Asn Asn Cys Met Asp Met Arg Arg Ser Ile Cys Tyr Arg

         Exon 16                              Exon 17
Gln Pro Cys Pro Ala Gln Asn Ser Ala Glu Tyr Gln Ala Leu Cys Ser Ser
```

FIG. 5C

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO:1:

TTAGCGTCCT ACACGAGC 18

(2) INFORMATION FOR SEQ ID NO:2:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO:2:

AGTGATCGTC ACTGCAGC 18

(2) INFORMATION FOR SEQ ID NO:3:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO:3:

TTGCCGGAAC ACAATTGGTT CC 22

(2) INFORMATION FOR SEQ ID NO:4:

(i) SEQUENCE CHARACTERISTICS:
(A) LENGTH: 25
(B) TYPE: nucleic acid
(C) STRANDEDNESS: single
(D) TOPOLOGY: linear (xi) SEQUENCE DESCRIPTION: SEQ ID NO:4:

ACGGTTGTCT TGTAAGTAGT CATAG 25

(2) INFORMATION FOR SEQ ID NO:5:

(i) SEQUENCE CHARACTERISTICS:
(A) LENGTH: 19
(B) TYPE: nucleic acid
(C) STRANDEDNESS: single
(D) TOPOLOGY: linear (xi) SEQUENCE DESCRIPTION: SEQ ID NO:5:

GAGCTACAAG TGATGTGTC 19

(2) INFORMATION FOR SEQ ID NO:6:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO:6:

CTCAACATTC TCGACTTCCT C 21

(2) INFORMATION FOR SEQ ID NO:7:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO:7:

GCAGACAAAA CTTCCAGGTG TGT 23

(2) INFORMATION FOR SEQ ID NO:8:

(i) SEQUENCE CHARACTERISTICS:
(A) LENGTH: 16
(B) TYPE: nucleic acid
(C) STRANDEDNESS: single
(D) TOPOLOGY: linear (xi) SEQUENCE DESCRIPTION: SEQ ID NO:8:

GTAGACTGTT CAGCAC 16

(2) INFORMATION FOR SEQ ID NO:9:

(i) SEQUENCE CHARACTERISTICS:
(A) LENGTH: 20
(B) TYPE: nucleic acid
(C) STRANDEDNESS: single
(D) TOPOLOGY: linear (xi) SEQUENCE DESCRIPTION: SEQ ID NO:9:

GATTGGTATG AACTGGACCG 20

(2) INFORMATION FOR SEQ ID NO:10:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO:10:

ACAGATGCGA ATGCTTCC 18

(2) INFORMATION FOR SEQ ID NO:11:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO:11:

GAATGTGAGA CTCCTGGAAT C 21

(2) INFORMATION FOR SEQ ID NO:12:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO:12:

CCAGTGTTGA TGCATTCC 18

(2) INFORMATION FOR SEQ ID NO:13:

(i) SEQUENCE CHARACTERISTICS:
(A) LENGTH: 20
(B) TYPE: nucleic acid
(C) STRANDEDNESS: single
(D) TOPOLOGY: linear -continued

```
    (xi) SEQUENCE DESCRIPTION:  SEQ ID NO:13:

CGATGTGGAT TTCAGACACC                                                 20

(2) INFORMATION FOR SEQ ID NO:14:

     (i) SEQUENCE CHARACTERISTICS:
          (A) LENGTH: 21
          (B) TYPE: nucleic acid
          (C) STRANDEDNESS: single
          (D) TOPOLOGY: linear

    (xi) SEQUENCE DESCRIPTION:  SEQ ID NO:14:

AGATTCCCGC GATCAGAAGC A                                               21

(2) INFORMATION FOR SEQ ID NO:15:

     (i) SEQUENCE CHARACTERISTICS:
          (A) LENGTH: 21
          (B) TYPE: nucleic acid
          (C) STRANDEDNESS: single
          (D) TOPOLOGY: linear

    (xi) SEQUENCE DESCRIPTION:  SEQ ID NO:15:

CCATTCCTAA CTGAGAGTTC C                                               21

(2) INFORMATION FOR SEQ ID NO:16:

     (i) SEQUENCE CHARACTERISTICS:
          (A) LENGTH: 21
          (B) TYPE: nucleic acid
          (C) STRANDEDNESS: single
          (D) TOPOLOGY: linear

    (xi) SEQUENCE DESCRIPTION:  SEQ ID NO:16:

GTGATTCTGA TTCATCCGTG G                                               21

(2) INFORMATION FOR SEQ ID NO:17:

     (i) SEQUENCE CHARACTERISTICS:
          (A) LENGTH: 22
          (B) TYPE: nucleic acid
          (C) STRANDEDNESS: single
          (D) TOPOLOGY: linear

    (xi) SEQUENCE DESCRIPTION:  SEQ ID NO:17:

TCCAGTCACC AACTGTCACT TC                                              22

(2) INFORMATION FOR SEQ ID NO:18:

     (i) SEQUENCE CHARACTERISTICS:
          (A) LENGTH: 22
          (B) TYPE: nucleic acid
          (C) STRANDEDNESS: single
          (D) TOPOLOGY: linear

    (xi) SEQUENCE DESCRIPTION:  SEQ ID NO:18:

GGTGGCACAA GTGTTCAATA GC                                              22
```

FIBRILLIN 1 GENE COMPRISING DUPLICATION MUTATION AND COMPOSITIONS AND KITS USING THE SAME

CROSS-REFERENCE TO RELATED APPLICATIONS

This application claims the benefit of U.S. Provisional Application No. 60/001,561 filed Jul. 22, 1995.

ACKNOWLEDGEMENT OF GOVERNMENT RIGHTS

This invention was made with Government support under NIH grant numbers AR32564 and DK45717. The Government may have certain rights in this invention.

FIELD OF THE INVENTION

The invention relates to genetic alterations within the Fibrillin 1 gene. The invention relates to diagnostic methods and reagents and kits for performing the same, animal modes of human diseases, and wound healing compositions and methods of using the same.

BACKGROUND OF THE INVENTION

Tight skin (Tsk) is an autosomal dominant mutation which occurred spontaneously in the inbred mouse strain B10.D2 (58N)/Sn; the original mutant was detected because it displayed unusually tight skin in the interscapular region (Green, M. C., et al. (1976). *Am. J. Pathol.* 82, 493–511.). Heterozygous Tsk mice have thickened skin which is firmly bound to the subcutaneous and deep muscular tissues and which lacks the pliability and elasticity characteristic of normal skin. Excessive accumulation of several collagens and glycosaminoglycans occurs in various organs including the skin, heart, and lungs (reviewed in Jimenez and Christner, (1994). *Clinics Derm.* 12, 425–436.). The Tsk mutation also results in larger skeletal size apparently caused by excessive growth of bone and cartilage. Homozygous Tsk/Tsk embryos degenerate in utero at ~8 days of gestation, whereas Tsk heterozygotes have a normal life span.

The Tsk mouse has been useful as a model for several human diseases. The increased expression of several collagen types found in the enlarged heart make Tsk/+ mice valuable models for the study of myocardial hypertrophy (Osborn, T. G., et al. (1987). *J. Biol. Cell. Cardiol.* 19, 581–587; Chapman, D., Eghbali, M. (1990). *Cardiovas. Res.* 24, 578–583; Bahey, R. I., et al. (1993) *Cardiovas. Res.* 27, 1061–1065). Heterozygous Tsk/+ mice serve as a model for human hereditary emphysema (Szapiel, S. V., et al. (1981). *Amer. Rev. Respir. Dis.* 123, 680–685; Rossi, G. A. et al. (1984) *Amer. Rev. Respir. Dis.* 129, 850–855; Gardi, C., et al. (1989). *Exp. Mol. Pathol.* 50, 398–410; Martorana, P. A., et al. (1989). *Am. Rev. Respir. Dis.* 139, 226–232). Tsk/+ mice have also been proposed as models for the hereditary connective tissue disorder, congenital fascial dystrophy, because the thickened fascia found in these patients resembles the subdermal thickening seen in Tsk/+ mice (Jablonska, S., et al. (1989). *J. Am. Acad. Derm.* 21, 943–950).

Another major interest in the Tsk mouse is that it has provided an animal model for the human disease Systemic Sclerosis or scleroderma (SSc). SSc is a connective tissue disease characterized by excessive extracellular matrix deposition in skin and various internal organs. It is generally accepted that SSc is an acquired disease, although a few instances of familial inheritance have been reported. The frequently progressive tissue fibrosis is largely responsible for the morbidity and mortality of patients with SSc. Although several animal models exist for the study of SSc, no one model reproduces all the features of the human disease. The effects of the Tsk mutation mimic the excessive accumulation of collagen in the dermis and some internal organ observed in patients with SSc. These abnormalities result from increased biosynthesis of collagen by Tsk fibroblasts. The Tsk mutation thus provides a unique opportunity to investigate the pathogenesis of tissue fibrosis at the molecular level.

There remains a need to discover the molecular nature of Tsk. There remains a need for methods of identifying individuals who have the genetic disorder associated with Tsk.

SUMMARY OF THE INVENTION

The present invention relates to methods of identifying duplication mutations in the fibrillin 1 (FBN1) gene.

The present invention relates to antisense compositions which selectively inhibit transcription or translation of genes with the duplication mutations in the fibrillin 1 gene, to pharmaceutical compositions comprising such antisense compositions and to methods of treating individuals with diseases caused by the duplication in the FBN1 gene.

The present invention relates to transgenic animals with mutated FBN1 genes, including those in which the gene is operably linked to an inducible or tissue specific promoter.

The present invention relates to wound healing compositions based on the local expression of the duplication mutations in the fibrillin 1 gene and reagents and kits for making the same as well as methods of treating individuals with chronic wounds.

DESCRIPTION OF PREFERRED EMBODIMENTS OF THE INVENTION

Figure 1:
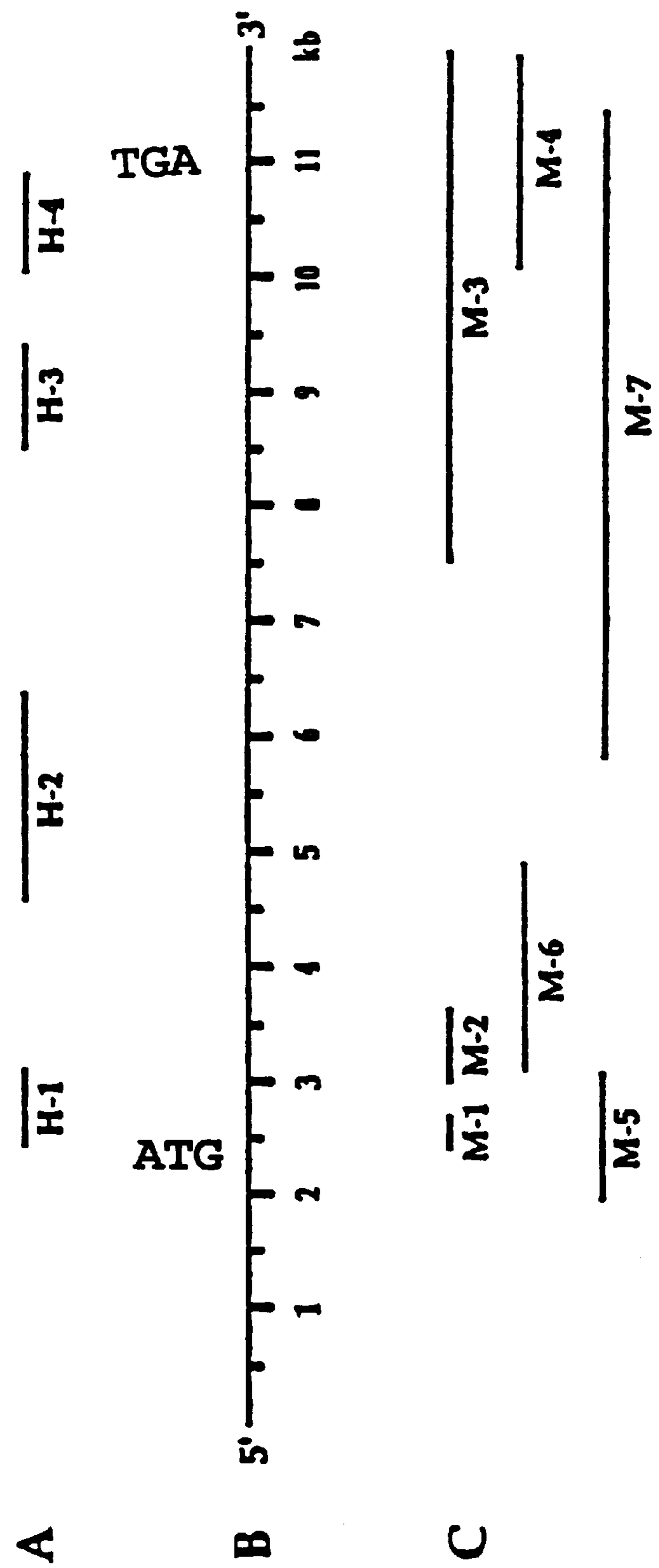
FIGS. 1(A–C) shows a schematic diagram of human FBN1 and mouse Fbn1 cDNA probes. The human probes (H-1 to H-4), shown next to the letter A, are presented with respect to a schematic diagram of the entire 12 kb mouse Fbn1 mRNA shown next to the letter B. The mouse Fbn1 cDNA clones (M-1 to M-7) shown next top the letter C were isolated as describe in the Results.

As used herein, the term "duplication-mutated FBN1 gene" is meant to refer to FBN1 genes, including human FBN1 genes, which contain a duplication of exons 17–40, or the coding region therein.

According to the invention, a specific mutation in the fibrillin 1 (FBN1) gene has been discovered to be associated with the tight skin (Tsk) mutation in mice. Tsk mice are models of human diseases, particularly, systemic sclerosis, scleroderma and stiff skin syndromes such as congenital facial dystrophy. It has been discovered that an in-frame 30–40 kb duplication which duplicates exons 17–40 of the 65 exon/350 kb FBN1 gene is responsible for Tsk. Repeats in corresponding portions of the homologous human FBN1 gene can be identified using diagnostic methodologies. Antisense compositions which selectively inhibit transcription or translation of genes with the Tsk-associated duplication can be used as therapeutics to treat individuals with diseases caused by the duplication in the FBN1 gene. Transgenic animals with mutated FBN1 genes, including those in which the gene is operably linked to an inducible or tissue specific promoter can be used to generate transgenic animal models of human diseases. Wound healing compositions and reagents and kits for making the same as well as methods of treating individuals with chronic wounds can be designed and made to include genetic constructs that have the duplication-mutated FBN1 gene.

To identify the gene responsible for the Tsk mutation, Tsk was mapped with respect to known molecular markers. The cumulative results localized Tsk to mouse chromosome 2, between B2m and Il1a, in a region syntenic with human chromosome 15. The gene encoding the extracellular matrix glycoprotein, fibrillin 1 (FBN1), resides within this region of synteny on human chromosome 15q21. Fbn1 was previously determined to lie between B2m and Il1a on a mouse chromosome 2 thus establishing its candidacy for the Tsk mutation (Goldstein, C., et al. (1994) *Mamm. Genome* 5, 696–700). The product of the FBN1 locus is a large 350 KDa secreted glycoprotein that provides a structural foundation for microfibril formation and elastin deposition, participates in the anchoring and biological functions of microfibrils, and may mediate protein-protein interactions and/or influence cell growth. The FBN1 structural locus encompasses 110 kb of genomic DNA; 65 exons encode the transcript, with most coding exons each representing a specific repeated domain (Pereira, L., et al. (1993) *Human Mol. Genet.* 2, 961–968, which is incorporated herein by reference). Mutations in FBN1 have been identified in patients with Marfan syndrome, a heritable connective tissue disease that primarily affects the cardiovascular, skeletal and ocular systems (Marfan, A. B. (1896). Bull. Mem. Soc. Med. Hop. Paris 13, 220–226; Dietz, H. C., et al. (1991) *Nature* 352, 337–339; Dietz, H. C., et al. (1992) *J. Clin. Invest.* 89, 1674–1680; Dietz, H. C., et al. (1992) *Hum. Mut.* 1, 366–374; Kainulainen, K., et al. (1992). *Proc. Natl. Acad. Sci. USA* 89, 5917–5921). In addition, mutations in FBN1 were recently described in patients with ectopia lentis and in infants exhibiting a neonatal lethal form of Marfan syndrome.

FBN1 has been mapped with respect to Tsk. The two loci are tightly linked. Mouse Fbn1 cDNA clones were used to probe Northern blots and a larger Fbn1 transcript was detected in Tsk mutants along with the normal transcript derived from the wildtype allele. Investigations of the genomic rearrangement responsible for the Tsk-specific FBN1 transcript revealed an internal duplication within the Fbn1 gene. The protein encoded by the mutant Fbn1 gene would contain an additional integrin binding (RGD) domain, 18 additional Egf-calcium binding (Egf-CB) motifs, one additional Fib1 motif, and two additional Tgf-binding protein (Tgf-bp) motifs. Our results clearly demonstrate the molecular basis of the Tsk mutation and lead to a unifying hypothesis to explain the pleiotropic and overtly diverse connective tissue alterations observed in Tsk mice as well as the recessive embryonic lethality of the Tsk mutation.

According to the present invention, methods, kits and reagents are provided which can be used to screen human individuals to determine if they possess a duplication-mutated FBN1 gene. Such mutations may be identified by a variety of well known techniques. The production of mRNA with the duplication may be detected, for example, using Northern blot analysis or RT-PCR. The production of abnormal fibrillin 1 that includes duplicated amino acid sequences may be detected, for example, using Western blot analysis or immunoassay. Genomic DNA may be analyzed to detect mutations by Southern blot analysis including restriction fragment length polymorphism analysis, oligonucleotide hybridization using allele specific probes or direct nucleotide sequencing of PCR amplified coding sequences.

Assays can be designed using these techniques to detect the presence or absence of duplication-mutated FBN1 genes, mRNA and gene products. The techniques for performing these analyses are well known to those having ordinary skill in the art and are generally described in Sambrook et al, eds. "Molecular Cloning: A Laboratory Manual" 2nd Edition, Cold Spring Harbor Laboratory Press 1989, which is incorporated herein by reference.

The human FBN1 gene is published in Maslen, C. L., et al. (1991). *Nature* 352, 334–337; Corson, G. M., et al. (1993) *Genomics* 17, 476–484; and Pereira et al (1993) *Human Mol. Genet.* 2, 961–968, which are each incorporated herein by reference. This information can be used to design probes, primers and antibodies useful to detect duplication-mutated FBN1 genes or gene products.

RNA may be extracted from tissue samples such as biopsy samples and analyzed by Northern blot analysis. Using probes which hybridize to both duplication-mutated FBN1 mRNA and normal FBN1 mRNA, Northern blot analysis provides the means to determine the presence of the larger duplication-mutated FBN1 RNA. Duplication-mutated FBN1 specific probes may also hybridize to duplication-mutated FBN1 genes at a distinguishable level from duplication-mutated FBN1 probes hybridizing to normal FBN1 genes. Known quantities of duplication-mutated FBN1 mRNA are used as controls. The present invention relates to kits for performing Northern blot analysis which comprise a container having a duplication-mutated FBN1 gene specific probe and instructions for performing the assay. Optionally, positive and/or negative controls may be provided and/or representative photos or diagrams of positive and/or negative results.

Similarly, the presence or absence of mRNA from the duplication-mutated FBN1 gene may be determined by RT-PCR. RNA is extracted from tissue samples such as biopsy samples and used in as substrate together with duplication-mutated FBN1 gene specific PCR primers in PCR reactions. If no nucleic acid molecules are amplified, the lack of duplication-mutated FBN1 mRNA is indicated. Known quantities of duplication-mutated FBN1 mRNA are used as controls. The present invention relates to kits for performing RT-PCR analysis which comprise a container having a duplication-mutated FBN1 gene specific primers and instructions for performing the assay. Optionally, positive and/or negative controls may be provided and/or representative photos or diagrams of positive and/or negative results.

Assays to detect the presence and/or quantity of duplication-mutated FBN1 gene encoded protein include Western blot and immunoassays. Cells from tissue samples or protein that is extracted from tissue samples such as biopsy samples are used. The presence and/or quantity of proteins that cross react with duplication-mutated FBN1 gene product can be determined with specific antibodies. Known quantities of duplication-mutated FBN1 gene product and/or normal FBN1 gene product may be used as controls. Western blot analysis is a technique whereby the presence of protein which is bound by FBN1 gene product specific antibodies can be detected and analyzed for size. Immunoassays do not measure protein size and duplication-mutated FBN1 gene product specific antibodies must be used. Western blot and immunoassay can be used to detect the presence of proteins encoded by duplication-mutated FBN1 gene as distinguished from proteins encoded by normal FBN1 genes. Duplication-mutated FBN1 gene product specific antibodies recognize epitopes generated due to the duplicated sequence. Such epitopes are not present on normal FBN1 gene product.

As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies. The production of antibodies and the protein structures of complete, intact antibodies, Fab fragments and $F(ab)_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, the duplication-mutated FBN1 gene product, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the duplication-mutated FBN1 gene product, the hybridoma which produces them is cultured to produce a continuous supply of antibodies.

The present invention relates to kits for performing Western blot analysis which comprise a container having an FBN1 gene product specific antibody and instructions for performing the assay. Additional immunoassay reagents may optionally be provided as described below. Optionally, positive and/or negative controls may be provided and/or representative photos or diagrams of positive and/or negative results.

The present invention relates to kits for performing Western blot analysis or immunoassay which comprise a container having a duplication-mutated FBN1 gene product specific antibody and instructions for performing the assay. Additional immunoassay reagents may optionally be provided as described below. Optionally, positive and/or negative controls may be provided and/or representative photos or diagrams of positive and/or negative results.

Genetic analysis of genomic DNA may be employed to detect duplication-mutated FBN1 genes. Some such analyses can be performed directly on extracted genomic DNA.

Other analyses include the amplification of the exons and adjacent sequences followed by analysis of the amplified DNA. In each case, an duplication-mutated FBN1 gene can be identified.

Southern blot analysis may be employed on extracted genomic DNA to identify the presence of nucleotide sequences that hybridize to FBN1 gene specific probes and for performing restriction fragment length polymorphism analysis to determine if a duplication-mutated FBN1 gene mutation is present.

Southern blot analysis may be employed on extracted genomic DNA to identify the presence of nucleotide sequences that hybridize to duplication-mutated FBN1 gene specific probes and for performing restriction fragment length polymorphism analysis to determine if a duplication-mutated FBN1 gene mutation is present.

The present invention relates to kits for performing Southern blot analysis including RFLP which comprise a container having a FBN1 gene specific probe and instructions for performing the assay. Optionally, positive and/or negative controls may be provided and/or representative photos or diagrams of positive and/or negative results.

The present invention relates to kits for performing Southern blot analysis including RFLP which comprise a container having a duplication-mutated FBN1 gene specific probe and instructions for performing the assay. Optionally, positive and/or negative controls may be provided and/or representative photos or diagrams of positive and/or negative results.

Oligonucleotide hybridization using duplication-mutated FBN1 gene specific probes can be used to determine the presence or absence of nucleotide sequences that hybridize to duplication-mutated FBN1 gene specific probes. Probes that hybridize to duplication-mutated FBN1 genes but that will not hybridize to the normal FBN1 genes can be used to detect the presence or absence of duplication-mutated FBN1 genes.

Isolated nucleic acid molecules that comprise a nucleotide sequence identical or complementary to a fragment of the FBN1 gene, particularly the portion of the coding sequence that is duplicated, that are at least 10 nucleotides are useful to practice the methods of the invention. In some embodiments, the isolated nucleic acid molecules consist of a nucleotide sequence identical or complementary to a fragment of the FBN1 gene, particularly the coding sequence, which is at least 10 nucleotides. In some embodiments, the isolated nucleic acid molecules comprise or consist of a nucleotide sequence identical or complementary to a fragment of the FBN1 gene, particularly the coding sequence, which is 15–150 nucleotides. In some embodiments, the isolated nucleic acid molecules comprise or consist of a nucleotide sequence identical or complementary to a fragment of the FBN1 gene, particularly the coding sequence, which is 15–30 nucleotides. Isolated nucleic acid molecules that comprise or consist of a nucleotide sequence identical or complementary to a fragment of the FBN1 gene, particularly the coding sequence, which is at least 10 nucleotides are useful as probes for identifying duplication-mutated FBN1 genes in genomic samples and cDNA sequence generated from RNA from samples, PCR primers for amplifying FBN1 genes and cDNA.

The nucleotide sequences in the FBN1 gene, particularly the coding sequence will be used to design probes, primers and complementary molecules which specifically hybridize to duplication-mutated FBN1 gene specific sequences.

The present invention also includes labelled oligonucleotides which are useful as probes for performing oligonucleotide hybridization methods to identify the presence or absence of duplication-mutated FBN1 gene sequences. Accordingly, the present invention includes probes that can be labelled and hybridized to specific nucleotide sequences of the duplication-mutated FBN1 gene. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a duplication-mutated FBN1 gene specific nucleotide sequence.

The present invention relates to kits for performing oligonucleotide hybridization analysis which comprise a container having a duplication-mutated FBN1 gene specific probe and instructions for performing the assay. Optionally, positive and/or negative controls may be provided and/or representative photos or diagrams of positive and/or negative results.

Genomic FBN1 gene sequences are amplified by PCR and analyzed to detect the presence or absence of duplication-mutated FBN1 gene sequence mutations. Genomic samples may be obtained from tissue, blood or other body fluids by routine collection methods. Chromosomal DNA is extracted and examined. The presence of duplication-mutated FBN1 genes can be detected.

In some embodiments, direct sequencing of duplication-mutated FBN1 gene sequences including some of those which are duplicated is performed following amplification of such sequences. A comparison of the sequence of amplified DNA to the known normal sequence indicates the presence or absence of mutations.

PCR may be used to amplify all or a portion of the genomic sequence that encode duplication-mutated FBN1 genes. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR primers are designed which amplify the region of the FBN1 gene that includes the site where duplication-mutated FBN1 gene mutations occur. Examples of PCR primers which will amplify sequences involved in duplication mutations are disclosed herein in Example 1, Experimental procedures section in the subsection entitled Probes, Primers and SSLP Analyses.

The present invention relates to kits for performing genomic DNA analysis which comprise a container having a set duplication-mutated FBN1 gene specific primers and instructions for performing the assay. Optionally, positive and/or negative controls may be provided and/or representative photos or diagrams of positive and/or negative results.

The present invention relates to a transgenic non-human mammal that comprises the recombinant expression vector that comprises a nucleic acid sequence that encodes the duplication-mutated FBN1 gene. The techniques for generating transgenic animals are well known. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which express duplication-mutated FBN1 gene. Preferred animals are rodents, particularly rats and mice. Such animals are useful as animal models to identify and characterize duplication-mutated FBN1 gene inhibitors. Effective duplication-mutated FBN1 gene product inhibitors will inactivate the duplication-mutated FBN1 gene product expressed by the transgene and the transgenic mice will revert to the phenotype similar to the parent line.

In some embodiments, transgenic animals include transgenes in which the duplication-mutated FBN1 gene is operably linked to a tissue specific and/or inducible promoter. Examples of tissue specific promoters include: type I collagen promoter which preferrentially expresses coding sequence in skin and lung (Jinminez, S. A. et al. 1994 *J. Biol. Chem.* 269:12684–12691; elastin promoter which expresses coding sequence in lung; and type IV collagen promoter which expresses coding sequence in vessel wall. These promoters can be used to generate transgenic mice that are specific models of human diseases.

The present invention relates to methods of and compositions for inhibiting the expression of duplication-mutated FBN1 genes in cells. The antisense oligonucleotides of the present invention can selectively inhibit duplication-mutated FBN1 genes but not FBN1 genes. The antisense oligonucleotides include single stranded DNA sequence and an antisense RNA oligonucleotide produced from an expression vector. Each of the antisense oligonucleotides of the present invention are complementary to regions of the duplication-mutated FBN1 mRNA sequence.

Ullrich et al., *EMBO J.,* 1986, 5:2503, which is incorporated herein by reference describes antisense technology. Oligonucleotides of the invention are preferably complementary to a nucleotide sequence that is 5–50 nucleotides in length, in some embodiments 8–40, more preferably 12–25 nucleotides, in some embodiments 10–15 nucleotides and in some embodiments 12–20 nucleotides.

The present invention is also directed to a method of inhibiting duplication-mutated FBN1 gene expression in mammals comprising contacting the mammal with an effective amount of an antisense oligonucleotide having a sequence which is complementary to a region of the duplication-mutated FBN1 mRNA.

Methods of administering the antisense oligos of the present invention include techniques well known in the art such as and not limited to liposomes, plasmid expression, or viral vector including retroviral vectors.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting duplication-mutated FBN1 gene expression. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty $\mu$g/ml antisense oligo was used for in vitro methods of providing oligos in media for cell growth in culture. This concentration may be extrapolated for in vivo use. The concentration of antisense oligonucleotides for in vivo use is about 40 $\mu$g/g body weight. The in vivo use of the expression vector expressing RNA oligonucleotides is determined by the number of transfected cells.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.,* 1986, 859, 88–94.

According to a preferred embodiment of the invention, human fibroblasts transfected with the FBN1 gene are prepared and used as wound healing compositions. Such compositions according to the invention are useful to treat individuals suffering from chronic wounds, particularly chronic wounds such as diabetic ulcers and pressure ulcers.

Compositions are prepared from fetal fibroblast cells, syngeneic fibroblast cells (i.e. matched donor cells) or autologous fibroblast cells (i.e. the patient's own cells). Fibroblasts may be obtained routinely using standard and well known techniques. An example of one such technique is described in Sly, W. S. and J. Grubb (1979) *Isolation of Fibroblasts from Patients* in *Methods of Enzymology, Vol. LVIII CELL CULTURE,* Jakoby, W. B. and I. H. Pastan, Eds. Ch. 38, pp. 444–450, which is incorporated herein by reference. Briefly, biopsy material is obtained by surgically removing a small section of skin and epidermal tissue, usually from the area of the arm below the shoulder or from the forearm. A biopsy punch is preferably used. The fibroblast cells are prepared by dividing pieces of the tissue, putting it on a tissue culture dish, covering it with a coverslip and tissue culture media. Cells are incubated in a $CO_2$ humidified incubator for about 10 days after which they are regularly fed fresh culture media. Within about 4–6 weeks cells may be split into multiple plates to expand cell numbers. Well known tissue culture techniques are also described in Butler, M. (1991) The characteristics and growth of cultured cells in *Mammalian Cell Biotechnology: A Practical Approach*, Butler, M., Ed. Ch. 1, pp. 1–26, which is incorporated herein by reference.

A gene construct is introduced into the cultured cells. The gene construct comprises a duplication-mutated FBN1 gene or a fragment thereof operably linked to a promoter which will function in a fibroblast cell, preferably a type 1 collagen promoter. The gene construct contains all necessary regulatory sequences such that the duplication mutated FBN1 gene or a fragment thereof will be expressed in the cells. The gene construct is introduced into cells using standard gene transfer techniques. Gene transfer techniques are well known and described in McDonald, C. (1991) Genetic engineering of animal cells in *Mammalian Cell Biotechnology: A Practical Approach*, Butler, M., Ed. Ch. 4, pp. 57–84, which is incorporated herein by reference.

Transfected cells are selected by standard techniques, such as by neomycin selection, and cultured to expand cell numbers of transfecting cells. In a preferred embodiment, the transfected cells are plated onto a biocompatible or biodegradable matrix which can be directly lifted and placed at the wound site. Examples of biocompatible matrices include nylon matrices, polyvinyl matrices, GORETEX® material matrices. Examples of biocompatible or biodegradable matrices are described in U.S. Pat. No. 5,376,118, U.S. Pat. No. 5,334,527, U.S. Pat. No. 4,703,108 and U.S. Pat. No. 4,645,669, which are incorporated herein by reference.

Wounds such as chronic wounds are easily identifiable. The wound may be debrided and a matrix containing 100,000 to 50,000,000 cells may be applied at the wound site. The wound is maintained clean and the transfected cells will grow over the wound site.

The present invention relates to wound healing kits which comprise a container having a gene construct that comprises a gene with the FBN1 duplication mutation or a fragment thereof operably linked to regulatory elements which will function in fibroblast cells and instructions for practicing the method of treating wounds. Optionally, the kit also includes biocompatible or briodegradable matrix material and/or a container with media for culturing cells and/or containers with reagents for transfecting cells and or containers for preparing the cells.

EXAMPLES

Example 1

Summary

Mice carrying the Tight skin (Tsk) mutation have thickened skin and visceral fibrosis due to excessive accumulation of extracellular matrix. These abnormalities have made Tsk/+ mice models for human scleroderma, hereditary emphysema and myocardial hypertrophy. We previously localized Tsk to mouse chromosome 2 in a region syntenic with human chromosome 15. The gene encoding the microfibrillar glycoprotein, fibrillin 1 (FBN1), which maps on human chromosome 15, provided a candidate gene for the Tsk mutation. We have discovered that the Tsk chromosome harbors a 30–40 kb genomic duplication within the Fbn1 gene that results in a longer Tsk-specific transcript. These findings provide a unifying hypothesis to explain the phenotype of Tsk/+ mice and the lethality of Tsk/Tsk embryos.

Results

Isolation of cDNA Clones Encoding the Murine FBN1 Gene

Probes specific for the human FBN1 gene (FIG. 1) were generated by RT-PCR of poly(A)$^{30}$ human lung RNA using the primers listed in Experimental Procedures. The radiolabeled human probes were used to screen a mouse lung cDNA library (Stratagene). All mouse cDNA clones isolated (FIG. 1) were sequenced and exhibited high homology to the corresponding human FBN1 sequences. The nucleotide coding and deduced amino acid sequences of mouse Fbn1 showed ≧95% identity with the correspond human FBN1 sequences. In addition, the mouse Fbn1 sequence we obtained was virtually identical to the recently published mouse sequence (Yin, W., et al. (1993) *J. Biol. Chem.* 270, 1798–1806).

Genetic Localization of the Fbn1 Gene with Respect to the Tsk Mutation on Mouse Chromosome 2

Genomic DNA from N2 progeny carrying the Tsk mutation derived from an intersubspecific backcross of [CAST xk (CAST×C57BL/6–pa+/+Tsk)F1] mice was subjected to Southern blot and PCR analyses to identify restriction fragment length polymorphisms (RFLPs) and simple sequence length polymorphisms (SSLPs). Our results originally defined a region between D2Mit63 and Il1a in which Tsk must reside. We previously mapped the mouse homolog of the human FBN1 gene to this same region between B2m and I on chromosome 2 using a different interspecific backcross. We considered Fbn1 a candidate based on its structure and function as well as on the similarities in organ systems (skeleton, heart, and occasionally lungs) affected in patients with Marfan syndrome and in Tsk/+ mice.

To directly investigate the genetic relationship of Fbn1 and Tsk, we mapped Fbn1 in the intersubspecific backcross involving CAST and C57BL/6(B6)–pa+/–Tsk mice. A 475 bp mouse Fbn1 cDNA probe from the 3' untranslated (UTR) region was used to screen parental genomic DNAs for RFLPs. The probe detected a 9.1 kb BclI fragment in B6–pa+/+Tsk mice and a 6.8 kb BclI fragment in CAST mice. To establish the position of Fbn1 with respect to Tsk, we typed those N2 progeny that showed recombinations between D2Mit63 and D2Mit19. A total of 132N2 progeny were typed for D2Mit63 and D2Mit19; 4 recombinant and 13 randomly selected nonrecombinant N2 progeny were typed for Fbn1. The results showed no recombination between Fbn1 and Tsk, indicating tight linkage of these two loci, and supported Fbn1 as a candidate for the Tsk mutation.

Northern Blot Analysis of Fbn1 Expression in Wildtype and Tsk/+ Mice

To further investigate the relationship of the Fbn1 gene to the Tsk mutation, we examined Fbn1 expression in different tissues of B6−++/++, B6−pa+/+Tsk and B6−pa+/pa+ mice. Total RNA was isolated and screened by Northern blot analysis with the M-3 probe. Selected mice were sex and age-matched to facilitate comparisons. A single transcript of 11 kb was detected in tissues of B6−++/+=and B6−pa+/pa+ mice. In contrast, two transcripts of 14 and 11 kb were detected in bt−pa+/+Tsk, b6−pa+/pa+, and a (CAST×B6) F1−$+^c+^c$/+Tsk mice was hybridized with the M-4 probe. The results showed that the 14 kb Fbn1 transcript is present only in mice carrying the Tsk mutation, regardless of genetic background.

Figure 2:
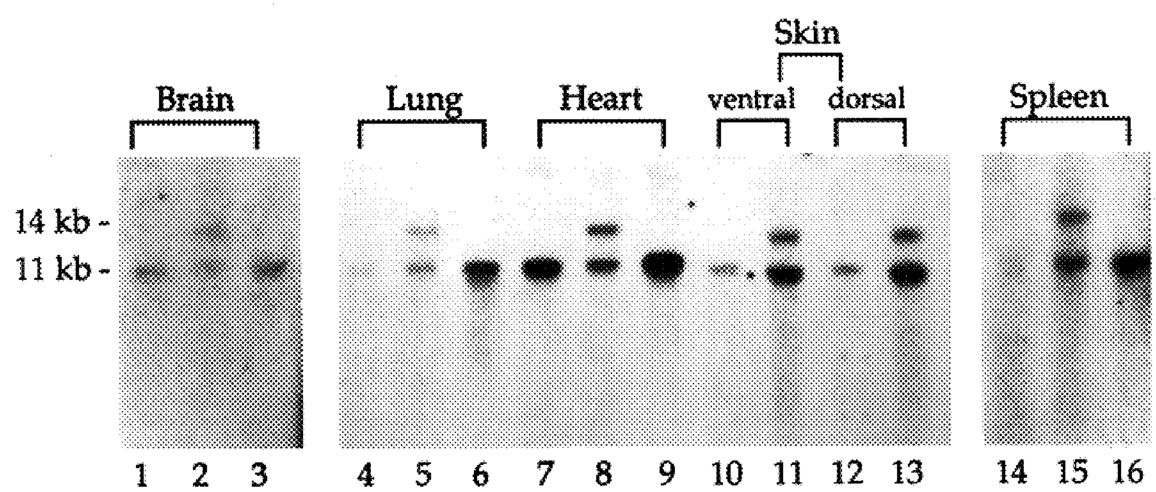
FIG. 2 shows results from a Northern blot analysis of Fbn1 expression in Tsk tissues. The expression pattern of Fbn1 was studied in tissues from 5-week old male Tsk/+ mice compared to sex and age-matched controls. Total RNA (10 $\mu$g/lane) from the tissues listed was hybridized with the M-3 probe. Lanes 1, 4, 7, 10, and 14 contain B6−++/++ RNA, Lanes 2, 5, 8, 11, 13 and 15 contain B6−pa+/+Tsk RNA, and Lanes 3, 6, 9, 12, and 16 contain B6−pa+/pa+ RNA. The length of autoradiographic exposure for brain and spleen was four times that for lung, heart and skin to enhance visualization of the low level of Fbn1 expression in these tissues.
Figure 3A:
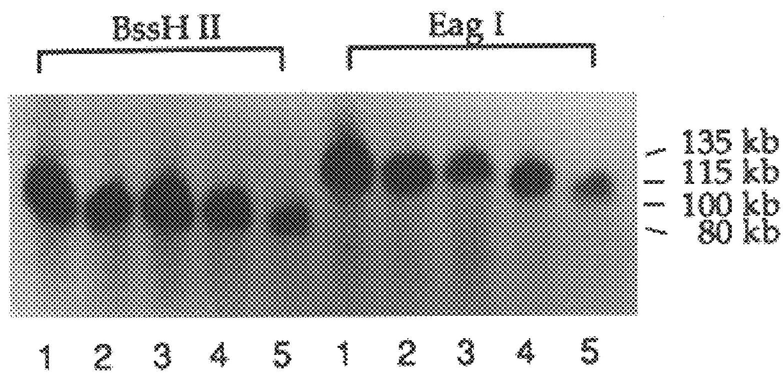
FIGS. 3(A–D) shows data from CHEF gel electrophoresis and a physical map of the genomic region containing the Fbn1 gene. In panel A, BssHiII and EagI were used to cleave genomic DNA from B6−pa+/pa+(Lane 1), B6−pa+/+Tsk (Lane 2), B6−++/++(Lane 3), (CAST X B6)−$+^c+^c$/+Tsk (Lane 4) and CAST $+^c+^c/+^c+^c$/(Lane 5) mice. The CHEF blots were hybridized with a 5' UTR region probe (panel A), a central coding region probe (panel B), and a 3' UTR region probe (panel C). Size fragments are listed to the right. The asterisks indicate Tsk-specific fragments. Panel D shows a physical map of the Fbn1 region was constructed by performing a series of single and double digestions of B6–pa+/pa+and B6–pa+/+Tsk genomic DNA. The + represents the physical map of the wildtype chromosome; the Tsk represents the physical map of the Tsk chromosome. Shown below both maps is the region encoding the Fbn1 gene; the direction of transcription is indicated by the arrow. Abbreviations used in panel D maps are B=BssHII, E=EagI, N=NotI, and R=NruI. Sequence analysis confirmed the presence of the B, E, R site in the 5' UTR region of the mouse Fbn1 gene. The scale bar indicates the fragment sizes with the exception of NotI (which are not drawn to scale). The NotI fragment is 660 kb from the + chromosome and 690 kb from the Tsk chromosome (Table 1).
Figure 3B:
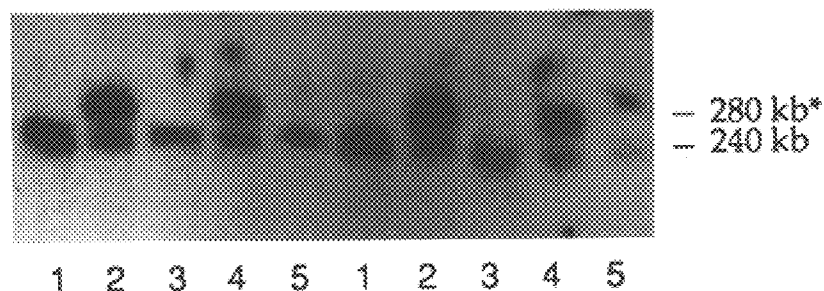
Figure 3C:
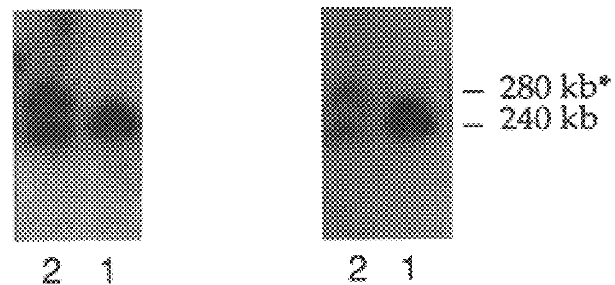
Figure 3D:
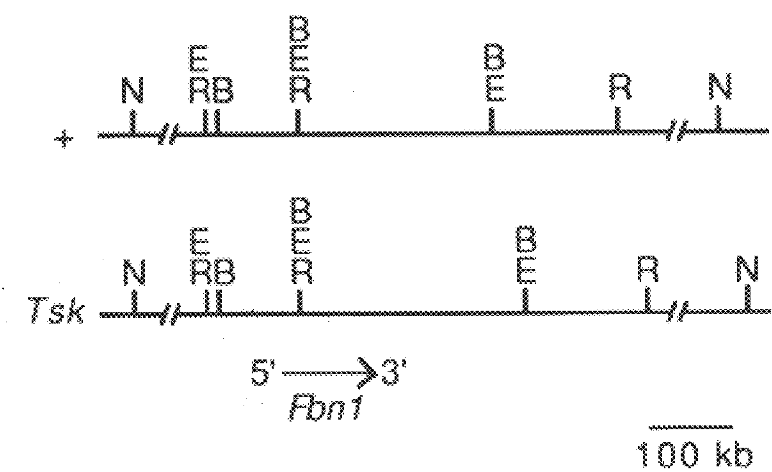

Northern blot analyses also revealed that the large 14 kb Tsk-specific transcript is detected in all tissues which normally express the 11 kb wildtype Fbn1 transcript. In addition, the expression levels of the Tsk-specific Fbn1 transcript paralleled the expression levels of the wildtype Fbn1 transcript in most tissues. Fbn1 expression levels were highest in dorsal and ventral skin, heart, and lungs, whereas Fbn1 expression levels were much lower in brain and spleen (FIG. 2). These findings suggested that the mutation responsible for the 14 kb Fbn1 transcript present in Tsk/+ mice did not alter the 5' promoter region of the Fbn1 gene. Moreover, tissues which show the greatest abnormalities in Tsk/+ mice (skin, heart, and lungs) also exhibit the highest levels of Fbn1 expression, supporting the hypothesis that the Tsk-specific Fbn1 transcript is responsible for and/or contributes to Tsk phenotypes. The expression level of the normal Fbn1 transcript appeared ~50% lower in mice heterozygous for Tsk compared to controls (FIG. 2). Taken together, these findings suggested that the normal 11 kb Fbn1 transcript originated from the wildtype chromosome whereas the mutant 14 kb Fbn1 transcript originated from the Tsk chromosome.

Pulsed Field Gel Electrophoresis Reveals an Alteration in the Fbn1 Genomic Region The physical relationship between the Fbn1 transcripts and the Tsk mutation was investigated by pulsed field gel electrophoresis. Genomic DNA from B6−pa+/+Tsk mice along with controls was digested with the rare cutting restriction endonucleases BssHII, EagI, NotI, or NruI and subjected to gel electrophoresis using contour-clamped homogeneous electric fields (CHEF) (FIG. 3). Fbn1 cDNA probes from the 5' UTR region, the central coding region, and the 3' UTR region were used for these analyses. Table 1 lists the restriction endonucleases and corresponding fragment sizes detected in Tsk/+ mice compared in controls. In each case, an abnormally large fragment was detected in Tsk mice with probes for the central coding and 3' UTR regions, but not with the probe for 5' UTR region. The mutant fragment present in Tsk/+ mice was 30–40 kb larger than the wildtype allele, regardless of the restriction endonuclease used (Table 1).

FIG. 3, panels A, B and C, show BssHII and EagI digested genomic DNAs from control and mutant mice hybridized to the 5' UTR region, central coding region, and 3' UTR region probes, respectively. The mutant fragments detected by the central coding region probe appeared twice as intense as the wildtype fragments, whereas the same mutant fragments detected by the 3' UTR probe appeared equal in intensity to the wildtype fragments (FIG. 3, panels B and C). This finding suggested that a duplication involving the region detected by the central coding region probe may have occurred within the Fbn1 gene.

A physical map of the genomic region encoding Fbn1 (FIG. 3, panel D) was established by performing a series of double digestions using BssHII, EagI, NotI, and NruI. Comparison of the maps for B6−pa+/pa+versus B6−pa+/+Tsk shows that although the BssHII, EagI, NruI and NotI cleavage sites 3' to the Fbn1 locus are in identical positions with respect to each other, these sites are separated by an additional 30–40 kb in the Tsk chromosome (FIG. 3, panel D). The data further supported the hypothesis of a duplication within the Fbn1 gene and indicated that 30–40 kb of genomic DNA was involved. To confirm this hypothesis, we screened genomic DNA by Southern blot analyses to define the limits of the putative duplicated region.

Identification of the Boundaries of the Duplication with the Fbn1 Gene

Based on the finding that only the central coding region probe detected a duplication and that the Tsk-specific Fbn1 transcript was ~3 kb larger than the wildtype Fbn1 transcript (FIG. 2), we reasoned that the duplication must also involve ~ kb of Fbn1 coding sequences. Therefore, genomic DNA from control and Tsk mice were screened to identify Tsk-specific restriction fragments by Southern blot analyses with probes that flanked both sides of the central coding region probe. These probes corresponded to fragments from clones M-6 and M-7 (FIG. 1).

Southern blots of genomic DNA from B6−++/++, B6−pa+/pa+, and B6−pa+/+Tsk mice digested with BamHI, BclI, BglI, DraI, EcoRI, EcoRV, HindIII, KpnI, MspI, PstI, PvuII, SacI, TaI, or XbaI were screened. Six probes that spanned the Fbn1 transcript corresponding to coordinates of ~3 kb to ~7 kb were tested (FIG. 1, panel C; Experimental Procedures). Probe B1/B2, which corresponds to bp 4283–4717, detected Tsk-specific fragments with BamHI, BclI, HindIII, KpnI, and PvuII. Probe T2/62, which corresponds to bp 7329–7862, detected Tsk-specific fragments with all restriction endonucleases tested except XbaI. BamHI, BclI, BglI, HindIII, and KpnI detected identical Tsk-specific fragments with both the B1/B2 and T2/62 probes, indicating that each fragment may represent eh single breakpoint fusion diagnostic for the duplication.

Figure 4A:
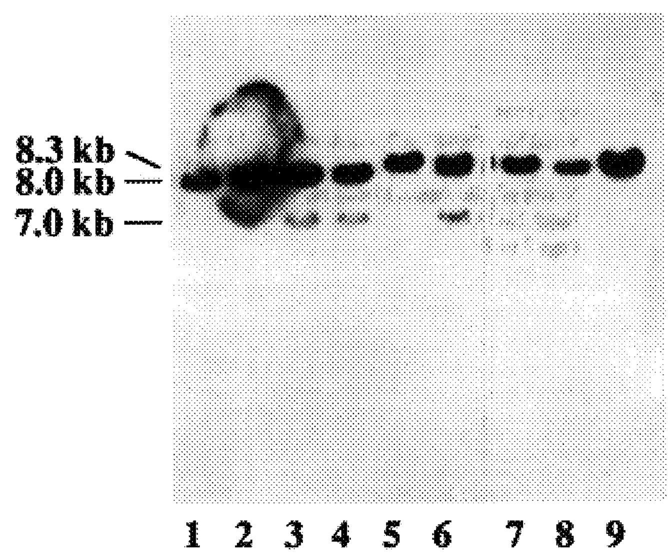
FIGS. 4(A–B) shows data confirming identification of a mutant breakpoint fusion fragment using Fbn1 cDNA probes. Southern blots of HindIII digested mutant and control genomic DNAs were hybridized with a series of Fbn1 cDNA probes including the B1/B2 (Panel A) and T3/62 (Panel B) probes. Lanes 1) B6–pa+/pa+male, 2) B6–++/++female, 3) B6–pa+/+Tsk male, 4) B6–pa+/+Tsk female, 5) CAST–$+^c+^c/+^c+^c$ female, 8) C57BL/10J–++/++ male, and 9) C57BL/10J–++/++ female. A Tsk-specific fragment of 7.0 kb is detected by both probes, whereas an endogenous 8.0 kb fragment is detected by the B1/B2 probe and endogenous fragments of 5.0, 3.5 and 1.8 kb are detected by the T2/62 probe in the inbred strains. CAST-specific fragments of 8.3, 3.4 and 1.8 kb are also detected. The B1/B2 and T2/62 probes distinguish the same unique 7.0 kb Tsk-specific fragment consistent with an internal duplication within the Fbn1 gene.
Figure 4B:
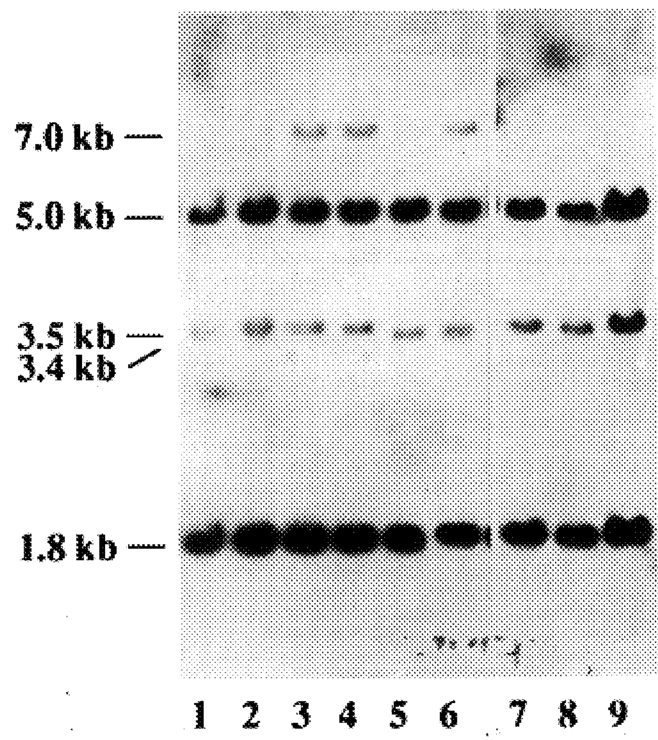

To prove that both probes detected a mutant 7.0 kb Tsk-specific HindIII fragment, we derived probes from either side of the breakpoint (corresponding to exon 40 for B1/B2 and exon 17 for T2/62; see below) and hybridized each to genomic DNA from mutant and control mice (FIG. 4). We tested the progenitors (C57BL/10 and DBA/2J) of the inbred strain (B10.D2(58N)/Sn) on which Tsk arose (Green et al., 1976). We also tested CAST−$+^c/+^c$, (CAST×B6)F1−$+^c+^c$/+Tsk, B6−pa+/+Tsk, B6−++/++, and B6=pa+/pa+ mice to prove that the 7.0 kb HindIII fragment was Tsk-specific and not the result of a polymorphism between strains. Both probes detected a common mutant Tsk-specific 7.0 kb HindIII fragment; however, the wildtype fragments detected by each probe were distinctly different, as expected for a duplication. The B1/B2 probe detected an 8.0 kb HindIII fragment in B6 and an 8.3 kb fragment in CAST (FIG. 4, panel A). The T2/62 probe detected 5.0, 3.5, and 1.8 kb HindIII fragments in B6 and 5.0, 3.4, and 1.8 kb fragments in CAST (FIG. 4, panel B). This finding indicated that although the B1/B2 and T2/62 probes are separated by 2612 bp in wildtype transcripts (which corresponds to 30–40 kb of genomic DNA based on the human FBN1 gene; Pereira et al., 1993), the probes reside in close proximity (≦7.0 kb) on the Tsk chromosome. Furthermore, the autoradiographic intensities of the 7.0 kb versus 8.0 kb or 8.3 kb fragments detected with the B1/B2 probe (FIG. 4, panel A) were consistent with a duplication that resulted in two copies of the wildtype fragment and only one copy of the breakpoint fusion fragment. Therefore, we concluded that the duplication must have occurred between bp 7445 and 4493 of the Fbn1 coding region.

Figure 5A:
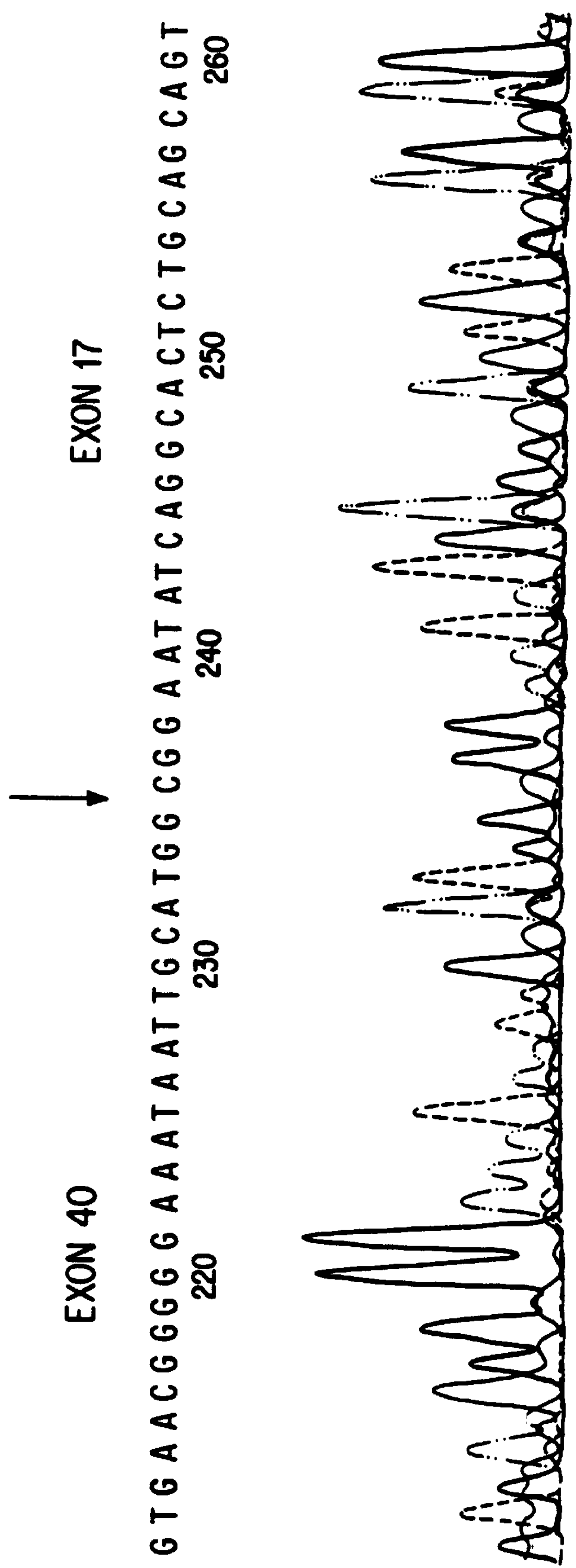
FIGS. 5(A–C) shows sequence analysis of the junction fragment within the Fbn1 transcript. RT of B6–pa+/+Tsk mRNA with primer B8 followed by PCR with primers D6 and B2 produced an 872 bp Tsk-specific product. Panel A shows data from sequencing of the RT-PCR product using primers D6 and B2 that revealed a unique fusion between bp 7445 and 4493 of the Fbn1 cDNA corresponding to a fusion between the end of exon 40 and the beginning of exon 17 as shown by the arrow. The sequence of the region immediately surrounding the fusion point is shown. Panel B shows the same sequence as in panel A, but shown in the double stranded form. The underlined amino acids shown in the upper line of panel C are the deduced translation product of the fusion. The middle line shows the translation of exons 40–41 in normal Fbn1 with the underlined residues in exon 40 being present in the fusion protein. The lower line shows the translation of exons 16–17 in normal Fbn1 with the underlined residues in exon 17 being present in the fusion protein. The alanine residue encoded by the fusion point is a $\frac{1}{3}$ split codon from exon 40 that joins the $\frac{2}{3}$ split codon from exon 17. The fusion leaves the open reading frame perfectly intact.

Sequence Analysis of the Fusion Fragment within the Tsk-specific Fbn1 Transcript RT-PCR was used to isolate and amplify a predicted unique Tsk-specific fragment resulting from the junction of duplicated Fbn1 coding segments. The B8 primer, corresponding to bp 4747–4724 of the Fbn1 cDNA, was used for the RT reaction. An 872 bp fragment was observed in B6–pa+/+Tsk mice but not in B6–pa+/pa+ mice, using the B2 and D6 primers for the PCR. Sequencing of the 872 bp fragment revealed that it contained sequences from two distinct regions of Fbn1 (FIG. 5). Since the intron/exon structure of the mouse Fbn1 gene is not known, we compared the fusion fragment to the intron/exon structure of the human FBN1 gene. The 5' portion of the fusion fragment corresponded to human exon 40 whereas the 3' portion corresponded to human exon 17, with the junction occurring between bp 7445 and 4493 of the Fbn1 cDNA (FIG. 5, panel A). The exact point of fusion leaves the nucleotides of both exons intact, and results in a mutant Fbn1 transcript that maintains the open reading frame and is 2952 bp larger than the normal Fbn1 transcript (FIGS. 5, panels B and C), consistent with the observed differences in transcript sizes. Thus, we predict that the large 14 kb Fbn1 transcript detected in Tsk/+ mice encodes a Fbn1 polypeptide that is 106 KDa larger than the normal 312 KDa Fbn1 polypeptide. The mutant Fbn1 protein has one additional RGD domain, two additional Tgf-bp repeats, 18 additional Egf-CB repeats, and one additional Fib motif in comparison to the wildtype Fbn1 protein.

The Fbn1 Gene Is Expressed Early During Mouse Embryogenesis

Previous in situ hybridization studies of sectioned mouse embryos indicated that Fbn1 was expressed at 8.5 days by mesometrial cells in the decidua and by endocardial cells in the embryo. In addition, the Fbn1 protein was detected by immunolabeling in Henson's node and the primitive groove of stage 3 avian embryos (Gallagher, B. C., et al. (1993) *Developmental Dynamics* 196, 70–78), which corresponds to preimplantation stages in mouse development. This finding suggested that Fbn1 expression in mammalian embryos may begin quite early in development. Furthermore, the mutant 14 kb Fbn1 transcript present in Tsk/+ mice would have to be expressed on or before day 8 of gestation to account for the degeneration of Tsk/Tsk embryos in utero. Therefore, we used an alternative and more sensitive approach to determine whether Fbn1 expression begins on or before the time of death of Tsk/Tsk embryos.

Figure 6A:
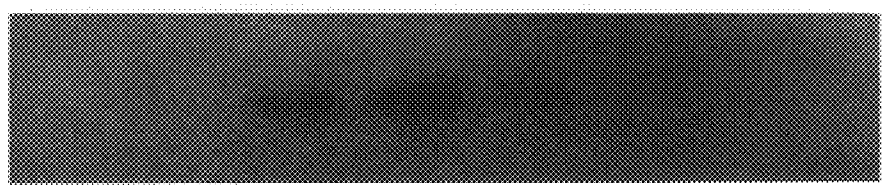
FIGS. 6(A–B) shows data indicating that the expression of the Fbn1 gene occurs in early mouse embryogenesis. PCR was used to amplify cDNA inserts from mouse libraries prepared from unfertilized eggs (Lane 1), 2-cell stage embryos (Lane 2), 8-cell stage embryos (Lane 3), blastocysts (Lane 4), 6.5 day ectoderm (Lane 5), 6.5 day endoderm (Lane 6), and a control with no template DNA (Lane 7). Panel A shows the 593 bp fragment identified by PCR of the cDNA libraries using primers 5UI and 5U4 followed by hybridization with radiolabeled primer 5U2. Panel B shows the 516 bp fragment identified by PCR of the cDNA libraries using primers 5U5 and 5U7 followed by hybridization with radiolabeled primer 5U6.
Figure 6B:
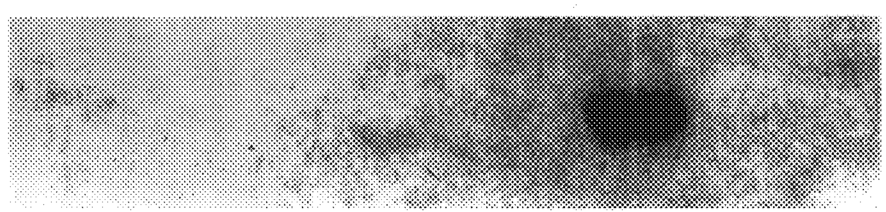

We screened mouse embryonic cDNA libraries prepared from poly(A)+ mRNA collected from unfertilized eggs, 2-cell stage embryos, 8-cell stage embryos, blastocysts, and 6.5 day embryonic ectoderm and endoderm. The libraries were amplified with two sets of PCR primers derived from the 5' URT region of the Fbn1 gene; PCR products were hybridized with another radiolabeled primer which resided between each of the two sets of primers to ensure specificity (see Experimental Procedures). Fbn1-specific products were detected in the 8-cell stage, blastocyst, 6.5 day embryonic ectoderm and endoderm libraries (FIG. 6, panels A and B). Although RT-PCT products specific for Fbn1 were not detected in the unfertilized egg or the 2-cell stage libraries, we cannot exclude the possibility that Fbn1 transcripts are expressed this early in development, but were not included by chance in the libraries. Overall the results demonstrate that Fbn1 is expressed as early as the 8-cell stage in mouse embryogenesis which is well before the time of death of Tsk/Tsk embryos.

Discussion

Our results demonstrate that the Tsk mutation is the result of an internal duplication with the Fbn1 gene. The 30–40 kb genomic duplication results in a larger than normal Fbn1 transcript in mice carrying the Tsk mutation. The mutant Fbn1 transcript contains a prefer in-frame duplication of exons 17–40, which presumably encodes a mutant 418 KDa polypeptide instead of the normal 312 KDa polypeptide. The duplication results in a significant disruption of connective tissue homeostasis that affects most organ systems in Tsk/+ mice.

The genomic duplication within the Fbn1 gene does not significantly influence the amounts of normal or mutant Fbn1 transcripts, as evidenced by comparable steady state levels of normal and mutant Fbn1 transcripts in all Tsk/+ tissues tested (FIG. 2). Thus, we predict that normal and mutant Fbn1 proteins are synthesized in Tsk/+ tissues. Since the Fbn1 protein is secreted, the presence of 984 additional amino acids might be expected to affect intracellular folding of the Fbn1 protein prior to secretion. However, the finding of increased amounts of microfibrils in Tsk/+ tissues suggests that Fbn1 secretion and incorporation into microfibrils is not significantly impaired. Therefore, mutant Fbn1 protein would be incorporated into microfibrils along with normal Fbn1 protein. The phenotypic alterations in Tsk/+ mice most likely arise because the mutant Fbn1 protein alters microfibril structure and function.

The Fbn1 Gene and Embryonic Lethality

Fbn1 expression was detected beginning at the 8-cell stage of embryogenesis (FIG. 6). Thus, normal Fbn1 expression begins prior to the degeneration and death of Tsk/Tsk embryos at day 8 and can account for the recessive embryonic lethality of the Tsk mutation. While the data indicate that normal Fbn1 protein is missing in Tsk/Tsk embryos, the tissues most immediately affected remain in question. Although the mutant Fbn1 transcript is most likely expressed within the embryo proper on or before the 8-cell stage, Tsk/Tsk embryos can survive at least until early post-implantation stages. Recent in situ hybridization studies show that Fbn1 expression is detectable in heart and mesometrial stromal cells of day 8.5 mouse embryos. In addition, studies in chicks suggest that Fbn1 delineates the primary axis of early embryos. Therefore, the critical time and place for microfibril formation may be in the embryo proper and/or the implantation site.

Comparison of Fbn1 Mutations in Marfan Syndrome with the Tsk Mutation

The Fbn1 protein is an integral structural component of 10–12 nm non-collagenous microfibrils present in the extracellular matrix of many organs and tissues (reviewed in Cleary, E. G. and M. A. (1983) *Int. Rev. Connect. Tiss. Res.* 10, 97–209). Fbn1 and the highly related Fbn2 (Lee, B., et (1991) *Nature* 352, 330–334; Zhang, H., et al. (1994). *J. Cell Biol.* 124, 855–863) proteins participate in the structure and assembly of microfibrils, acting as templates for tropoelastin deposition in elastic tissues, and provide anchoring roles in non-elastic tissues. The fibrillins are involved in the biological functions of microfibrils and have been proposed to regulate cellular activities and morphogenetic programs.

The variety of FBN1 mutations found in patients with Marfan syndrome are providing an understanding of the relationship between genotype and the variability and severity of the clinical manifestations of the disease. The mutations described include 1) genomic deletions and nonsense mutations that induce exon skipping, resulting in shortened or truncated FBN1 proteins, 2) specific nonsense mutations that result in decreased levels of mutant FBN1 transcripts, and 3) missense mutations that alter the function of the FBN1 protein. Studies of FBN1 synthesis and secretion in cultured fibroblasts from Marfan syndrome patients have revealed potential mechanisms by which specific FBN1 mutations in Marfan syndrome (Aoyama, T., et al. (1993) *Hum. Mol. Genet.* 2, 2135–2140; Aoyama, T., et al. (1993) *J. Clin. Invest.* 94, 130–137). The mechanisms include the mutant protein 1) interfering with secretion of FBN1, 2) interfering with normal microfibril formation, 3) being incorporated into microfibrils along with normal protein, causing a disruption in microfibril structure and/or function, and 4) severely decreased levels of mutant FBN1 transcripts result in similarly low levels of FBN1 protein, causing an overall reduction in the amount of microfibrils formed. Most of these mechanisms involve the mutant FEN1 protein acting in a dominant negative fashion to cause various disease phenotypes.

The similarities and differences between the phenotypes observed in patients with Marfan syndrome and mice carrying the Tsk mutation can now be understood at the molecular level. The loose connective tissue of patients with Marfan syndrome (reviewed in Godfrey, 1993) is in contrast to the thickened dermis and fascia exhibited by Tsk/+ mice. The skeletal alterations of Marfan syndrome include an elongated and disproportionate skeleton with long extremities, arachnodactyly, spinal scoliosis, and joint hypermobility. Tsk/+ mice have an enlarged but mostly well proportioned skeleton, due to excessive growth of bone and cartilage; shortened tendons and hyperplasia of tendon sheaths were also noted. The cause of morbidity and mortality in Marfan syndrome patients is due to structural abnormalities in the cardiovascular system which include aortic root dilatation, mitral valve prolapse, aortic regurgitation and aneurisyms. The heats of Tsk/+ mice are enlarged as a result of myocardial fibrosis, but in contrast to Marfan syndrome, vessel walls are thicker than normal. No cutaneous or visceral fibrosis has been demonstrated in patients with Marfan syndrome, whereas the skin and other organs of Tsk/+ mice display excessive accumulation of extracellular matrix molecules including collagen (types I, III, IV, and VI), glycosaminoglycans, and fibronectin. Some Marfan syndrome patients develop pulmonary emphysema, whereas Tsk/+ mice develop an emphysema-like condition with morphological distortion of lung tissue and progressive elastolytic changes by one month of age.

It is the dysfunction, disruption or decrease of FBN1 deposition that leads to Marfan syndrome in humans. In contrast, the increased amounts of microfibrils found in the connective tissue of Tsk/+ mice provide an imperfect matrix (formed from normal and mutant Fbn1 protein), that can directly or indirectly result in induction of a generalized fibrotic response. These findings lead to the conclusion that the Tsk-specific Fbn1 protein is not acting in a dominant negative fashion (as in the case for Marfan syndrome), but rather that the mutant Fbn1 protein is acting as a dominant gain-of-function mutation in Tsk tissues. Thus, alterations in Fbn1 can lead to a diverse range of disease phenotypes depending on the location and nature of the mutation.

The Contribution of a Mutant Fbn1 Glycoprotein to Tsk Phenotypes

The large Tsk-specific Fbn1 transcript encodes a mutant Fbn1 protein that contains several additional domains, each of which may be contributing to the phenotypes exhibited by Tsk mice. The mutant Fbn1 protein has one additional RGD domain. The RGD domain is responsible for anchoring cells to the microfibrillar network and has a role in cell adhesion, migration and differentiation. The presence of a second RGD domain could influence cell adhesion and/or cell shape by modifying integrin binding. Alternatively, incorporation of the mutant Fbn1 protein into microfibrils may lead to aberrant signals being transmitted to adjacent cells. These changes could trigger intracellular signals that govern a cascade of events ultimately resulting in the synthesis of increased amounts of extracellular matrix molecules. Alterations in integrin binding can also trigger autoimmune responses, and may be involved in the subsequent production of autoantibodies observed in Tsk/+ mice.

The Egf-CB motif binds calcium and is important for maintaining and stabilizing microfibrillar structure and function. The packing of fibrillin monomers and the structural integrity of microfibrils is dependent on calcium binding by Egf-CB domains. However, these domains may also be important for binding of other proteins to the extracellular matrix that convey augmented signals to neighboring cells.

The Tgf-β family of proteins play critical roles in development, inhibition of cell proliferation, differentiation, wound healing, inflammation, and fibrosis. The presence of two additional Tgf-bp domains within each mutant Fbn1 protein may result in enhanced activity of Tgf-β, a pleiotropic cytokine that has potent fibrogenic effects. In addition, the Fbn1 protein bears striking structural similarities to the latent Tgf-β binding proteins, LTBP1, LTBP2 and Ltbp3, especially in the region of the duplication. These proteins are part of large multiprotein complexes that bind intracellular Tgf-β1 and sequester its action until the latent complex is secreted and targeted to specific extracellular matrixes or tissues. Ltbp proteins have a critical role in the association of Tgf-β with the extracellular matrix and are thought to be involved in the release of latent Tgf-β from the matrix as well. The mutant Fbn1 protein may mimic the action of Ltbp proteins by participating in the assembly and secretion of latent Tgf-β, or in the binding of Tgf-β1 to the matrix, thus resulting in the excessive Tgf-β activity that can lead to the cutaneous and visceral fibrosis observed in Tsk/+ mice.

Experimental Procedures

Mice

Inbred mice of the Mus castaneus (CAST/Ei)–$+^c+^c/+^c+^c$, B6–++/++, B6–pa+/pa+ and B6–pa+/+Tsk strains were purchased from The Jackson Laboratory (Bar Harbor, Me.). Mice carrying Tsk and pa were maintained at the Jefferson Medical College (Philadelphia, Pa.). The intersubspecific backcross of [CAST×(CAST×B6–pa+/+Tsk)] mice was as described (Siracusa et al., 1993). Only N2 progeny displaying the mutant Tsk phenotype, as determined by manual assessment of the thickness and tightness of the skin in the interscapular region, were used.

Probes, Primers and SSLP Analyses

The human probes H-1, H-3 and H-4 were generated by RT-PCR of human lung fibroblast RNA using primers based on the published human sequence. H-1 primers were 5'TTAGCGTCCTACACGAGC3' (SEQ ID NO:1) (182–200 bp) and 5'AGTGATCGTCACTGCAGC3' (SEQ ID NO:2) (551–533 bp). H-3 primers were 5'TTGCCGGAACA-CAATTGGTTCC3' (SEQ ID NO:3) (5845–5866 bp) and 5'ACGGTTGTCTTGTAAGTAGTCATAG3' (SEQ ID NO:4) (6653–6629 bp). H-4 primers were 5'GAGCTA-CAAGTGATGTGTC3' (SEQ ID NO:5) (8014–8033 bp) and 5'CTCAACATTCTCGACTTCCTC3' (SEQ ID NO:6) (8471–8492 bp). Poly(A)+ human lung RNA was a gift from Dr. Arturo Diaz (Jefferson Medical College, Philadelphia, Pa.). The H-2 probe was described previously in (Goldstein et al., 1994 Supra). The fusion sequence was obtained by RT-PCR using the Superscript Preamplication System for First Strand Synthesis kit (Gibco-BRL). The primer for the RT reaction B8 5'GCAGACAAAACTTCCAGGTGTGT3' (SEQ ID NO:7) (4747–4724 bp). The primers used for the PCR reaction were B2 5'GTAGACTGTTCAGCAC3' (SEQ ID NO:8) (4700–4684 bp) and D6 5'GATTGGTAT-GAACTGGACCG3' (SEQ ID NO:9) (6798–6818 bp). Additional primers for these studies were B1 5'ACAGAT-GCGAATGCTTCC3' (SEQ ID NO:10) (4283–4299 bp), T2 5'GAATGTGAGACTCCTGGAATC3' (SEQ ID NO:11) (7330–7350 bp), and 62 5'CCAGTGTTGATGCATTCC3' (SEQ ID NO:12) (7862–7845 bp). Primers were prepared using an Applied Biosystems Model 394 DNA Synthesizer.

Isolation of cDNA Clones and DNA Sequencing

A 6–8 week old (B6×CBA) F1 female mouse lung cDNA library (Stratagene) was screened with the human cDNA probes (H-1 to H-4) hybridized at 64° C. Seven clones (M-1 to M-7) were isolated and sequenced from both directions using the Taq DyeDeoxy Terminator Sequencing kit (Applied Biosystems, Inc.) on an Applied Biosystems Model 373A DNA Sequencer.

Southern and Northern Blot Analyses

Genomic DNA extractions, restriction endonuclease digestion, agarose gel electrophoresis, Southern blot transfer and washes as well as total RNA was isolated from mouse tissues using the guanidine isothiocyanate method and size-fractionated by electrophoresis through 6.3% formaldehyde, 1.2% agarose gels in 1×MOPS running buffer were performed. The DNA and RNA was transferred to Hybond N+ nylon membranes (Amersham) by blotting in 10× or 20×SSC, respectively. Membranes were hybridized overnight at 65° C., washed in 1×SSC at 65° C. for 1 hr, and exposed to Kodak XAR5 autoradiography film. Probes were $^{32}$P-labeled using a random prime kit (Boehringer Mannheim).

Pulsed-field Gel Electrophoresis

Agarose embedded single cell suspensions from spleen were prepared and digested with restriction endonucleases. Yeast and Lambda DNA-PFGE markers were the molecular weight size standards (Pharmacia). CHEF gel electrophoresis used 1% Rapid agarose (Gibco-BRL) in 0.5×TBE and run in a pulsed-field system (C.B.S. Scientific) at 120–130V for 40–42 hrs. Gels were stained with EtBr, photographed, and nicked for 5 min at wavelength 254 nm. Denaturation, neutralization, transfer, hybridization and washing were as described above for Southern blots, except that the transfer lasted two days.

Screening of Embryonic Libraries for Fbn1 Expression

Mouse embryo cDNA libraries were a gift from Dr. Jay Rothstein (Jefferson Cancer Institute, Philadelphia, Pa.). Each library was subjected to PCR using 20 μg M1uI and Sa1I-digested cDNA (to linearize the inserts), 50 ng each prior, 0.125 mM each dNTP, 1×PCR buffer and 1 u Taq polymerase (Boehringer Mannheim) in a 20 μl reaction. Two sets of primers from the 5' UTR region of the Fbn1 gene were used for amplification and a third primer that resided between each original pair was hybridized to the PCR products. The first primer pair was 5U5 5'CGATGTG-GATTTCAGACACC3' (SEQ ID NO:13) (681–701 bp) and 5U7 5'AGATTCCCGCGATCAGAAGCA3' (SEQ ID NO:14) (1197–1177 bp); resulting products were hybridized to 5U6 5'CCATTCCTAACTGAGAGTTCC3' (SEQ ID NO:15) (790–810 bp). The second primer pair was 5U1 5'GTGATTCTGATTCATCCGTGG3' (SEQ ID NO:16) (65–85 bp) and 5U4 5'TCCAGTCACCAACTGT-CACTTC3' (SEQ ID NO:17) (658–637 bp); resulting products were hybridized to 5U2 5'GGTGGCACAAGTGT-TCAATAGC3' (SEQ ID NO:18) (90–111 bp). PCR conditions were an initial denaturation at 94° C. for 4 min followed by 30 cycles of 94° C. for 30 sec, 63° C. for 30 sec, 72° C. for 30 sec, and ended with one cycle of 72° C. for 7 min. Resulting PCR products were electrophoresed on 1.2% agarose gels in 1×TBE at 100V for 3 hrs and transferred to Hybond N+ nylon membranes. Oligonucleotide hybridization was 50° C. using each internal primer end-labeled with $\lambda^{32}$P-dATP by T4 Polynucleotide kinase (Promega). Blots were washed twice in 6×SSCP, 0.1% SDS for 25 min at 42° C. and exposed to Dupont NEN Reflection film.

TABLE 1

Size of long-range restriction endonuclease fragments detected by Fbn1 cDNA probes[a]

| | BssHII | EagI | NotI | NruI |
|---|---|---|---|---|
| A) 5' untranslated region probe | | | | |
| CAST−+[c]/+[c] | 80[b] | 115[b] | 690 | 115[b] |
| (CASTxB6) F1 − sk/+[c] | 100 | 135 | 690 | 135 |
| | 80[b] | 115[b] | | 115[b] |
| C57BL/6J−++/++ | 100 | 135 | 690 | 135 |
| B6-pa+/+Tsk | 100 | 135 | 690 | 135 |
| B6-pa +/pa+ | 100 | 135 | 690 | 135 |
| B) Central coding region probe | | | | |
| CAST-+[c]/+[c] | 240 | 240 | 660 | 395 |
| (CASTxB6) F1 − Tsk/+[c] | 280[c] | 280[c] | 690[c] | 430[c] |
| | 240 | 240 | 660 | 395 |
| C57BL/6J − ++/++ | 240 | 240 | 660 | 395 |
| B6-pa +/+Tsk | 280[c] | 280[c] | 690[c] | 430[c] |
| | 240 | 240 | 660 | 395 |
| B6-pa +/pa+ | 240 | 240 | 660 | 395 |
| C) 3' untranslated region probe | | | | |
| CAST−+[c]/+[c] | 240 | 240 | 660 | 395 |
| (CASTxB6) F1 − Tsk/+[c] | 280[c] | 280[c] | 690[c] | 430[c] |
| | 240 | 240 | 660 | 395 |
| C57BL/6J − ++/++ | 240 | 240 | 660 | 395 |
| B6-pa +/+Tsk | 280[c] | 280[c] | 690[c] | 430[c] |
| | 240 | 240 | 660 | 395 |
| B6-pa +/pa+ | 240 | 240 | 680 | 395 |

[a]All fragment sizes are given in kb.
[b]These fragments are CAST-specific.
[c]These fragments are Tsk-specific.

We claim:

1. An isolated human fibroblast cell comprising a gene construct, said gene construct comprising a duplication mutated fibrillin 1 gene operably linked to regulatory elements that are functional in said cell wherein said cell expresses said duplication mutated fibrillin 1 gene.

2. The human fibroblast cell of claim 1 wherein said cell is a fetal cell.

3. The human fibroblast cell of claim 1 wherein said duplication mutated fibrillin 1 gene is operably linked to a type I collagen promoter.

4. A composition comprising isolated human fibroblast cells according to claim 1.

5. The composition of claim 4 wherein said cells are on a biocompatible or biodegradable matrix.

6. The composition of claim 4 comprising 100,000 to 50,000,000 cells.

7. A method of treating a wound comprising applying a composition of claim 4 to said wound.

8. The method of claim 7 wherein said cells are on a biocompatible or biodegradable matrix.

9. The method of claim 7 wherein said composition comprises 100,000 to 50,000,000 cells.

10. A wound healing kit comprising a container having a gene construct that comprises a duplication mutated fibrillin 1 gene operably linked to regulatory elements that are functional in an isolated fibroblast cell and instruction for transfecting said isolated fibroblast cell with said gene construct for the preparation of a wound healing composition to be applied to a wound.

11. The kit of claim 10 further comprising a biocompatible or biodegradable matrix.

* * * * *